(12) United States Patent
Inada

(10) Patent No.: US 8,866,736 B2
(45) Date of Patent: Oct. 21, 2014

(54) GAZE DETECTION APPARATUS AND METHOD

(75) Inventor: Junya Inada, Nagoya (JP)

(73) Assignee: DENSO CORPORATION, Kariya (JP)

(*) Notice: Subject to any disclaimer, the term of this patent is extended or adjusted under 35 U.S.C. 154(b) by 228 days.

(21) Appl. No.: 13/360,916

(22) Filed: Jan. 30, 2012

(65) Prior Publication Data
US 2012/0200490 A1  Aug. 9, 2012

(30) Foreign Application Priority Data

Feb. 3, 2011 (JP) .................................. 2011-21801

(51) Int. Cl.
| | | |
|---|---|---|
| B60R 11/04 | (2006.01) | |
| G01C 21/26 | (2006.01) | |
| G06T 1/00 | (2006.01) | |
| A61B 3/113 | (2006.01) | |
| G08G 1/16 | (2006.01) | |
| G01B 11/00 | (2006.01) | |

(52) U.S. Cl.
CPC ................. *A61B 3/113* (2013.01); *B60R 11/04* (2013.01); *G01C 21/26* (2013.01); *G06T 1/00* (2013.01); *G08G 1/16* (2013.01); *G01B 11/00* (2013.01)
USPC .......................................... 345/156; 345/166

(58) Field of Classification Search
CPC ........ A61B 3/113; B60R 11/04; G01B 11/00; G01C 21/26; G06T 1/00; G08G 1/16
See application file for complete search history.

(56) References Cited

U.S. PATENT DOCUMENTS

| | | | | |
|---|---|---|---|---|
| 5,859,642 | A * | 1/1999 | Jones ............................ | 715/821 |
| 5,898,423 | A * | 4/1999 | Tognazzini et al. ........... | 345/158 |
| 6,091,378 | A * | 7/2000 | Richardson et al. ............. | 345/7 |
| 6,433,759 | B1 * | 8/2002 | Richardson et al. ............. | 345/7 |
| 6,437,758 | B1 * | 8/2002 | Nielsen et al. .................... | 345/8 |
| 2010/0165093 | A1* | 7/2010 | Sugio et al. ..................... | 348/78 |
| 2010/0182232 | A1* | 7/2010 | Zamoyski ..................... | 345/157 |
| 2012/0105486 | A1* | 5/2012 | Lankford et al. ............. | 345/661 |

(Continued)

FOREIGN PATENT DOCUMENTS

| | | |
|---|---|---|
| JP | A-H02-185230 | 7/1990 |
| JP | A-H7-035543 | 2/1995 |

(Continued)

OTHER PUBLICATIONS

Office Action mailed Jan. 29, 2013 in corresponding JP Application No. 2011-021801 (and English translation).

(Continued)

*Primary Examiner* — Claire X Pappas
*Assistant Examiner* — Richard Hong
(74) *Attorney, Agent, or Firm* — Posz Law Group, PLC

(57) ABSTRACT

A gaze detection apparatus is disclosed. The gaze detection apparatus includes: a gaze detection section that detects gaze of a target person; a display section that includes a display screen for displaying an image; a gaze position determination section that determines, based on a result of detection by the gaze detection section, whether or not the display screen lies in the gaze of the target person; and a first display control section that displays a first detection result image at an intersection point between the gaze of the target person and the display screen when the first gaze position determination section determines that the display screen lies in the gaze of the target person.

9 Claims, 10 Drawing Sheets

(56) References Cited

U.S. PATENT DOCUMENTS

| | | | |
|---|---|---|---|
| 2012/0215403 A1* | 8/2012 | Tengler et al. | 701/36 |
| 2012/0242591 A1* | 9/2012 | Kawalkar | 345/173 |
| 2013/0135198 A1* | 5/2013 | Hodge et al. | 345/156 |
| 2013/0176208 A1* | 7/2013 | Tanaka et al. | 345/156 |
| 2013/0187845 A1* | 7/2013 | Madau et al. | 345/156 |

FOREIGN PATENT DOCUMENTS

| | | | | |
|---|---|---|---|---|
| JP | A-H7-329657 | | 12/1995 | |
| JP | A-H09-212082 | | 8/1997 | |
| JP | H09-212082 | * | 8/1997 | G09B 29/00 |
| JP | A-H9-238905 | | 9/1997 | |
| JP | A-2007-045169 | | 2/2007 | |
| JP | A-2009-015533 | | 1/2009 | |
| JP | A-2010-039933 | | 2/2010 | |
| JP | A-2010-100260 | | 5/2010 | |
| JP | A-2010-126135 | | 6/2010 | |
| JP | A-2010-165087 | | 7/2010 | |

OTHER PUBLICATIONS

Ishikawa, Takahiro et al. "Passive Driver Gaze Tracking With Active Appearance Models." *Proceedings of the 11$^{th}$ World Congress on Intelligent Transportation System* (Oct. 2004): 1-12.

* cited by examiner

GAZE DETECTION APPARATUS AND METHOD

CROSS REFERENCE TO RELATED APPLICATION

The present application is based on and claims priority to Japanese Patent Application No. 2011-21801 filed on Feb. 3, 2011, disclosure of which is incorporated herein by reference.

TECHNICAL FIELD

The present disclosure relates to a gaze detection apparatus and method for detecting a gaze of person.

BACKGROUND

A technique for detecting a gaze of a driver of a vehicle in order to assist the driver's driving is known. For example, there is a technique for detecting a gaze of a driver who is driving a vehicle, and for determining whether or not the driver is inattentive in driving (i.e., inattentive driving). When it is determined that the driver's driving is inattentive driving, a warning sound is outputted (see Patent Document 1 for example).

In order to detect the gaze, it is necessary to perform calibration for minimizing a gap between a detected direction of gaze and an actual direction of gaze. This calibration may be performed upon satisfaction of a predetermined condition. For example, when a location of the driver gazing object is identified, a gaze detection method is corrected, so that the driver gazing object lies in the detected direction of gaze (for example, see Patent Documents 2 and 3). For example, when a driver manipulates an operation switch in a vehicle compartment, it can be determined that the driver's eye is fixed to this operation switch.

When a driver conducts an operation to start the calibration, an image for gaze is displayed at a predetermined place and a gaze detection method is corrected, so that the gaze image lies in the detected direction of gaze (see Patent Document 4 for example).

Patent Document 1: JP-2010-39933A1
Patent Document 2: JP-H9-238905A1
Patent Document 3: JP-2009-15533A1
Patent Document 4: JP-H7-35543A1

According to the technique described in Patent Documents 2 and 3, the calibration can be performed while the driver is being unaware of whether or not the calibration is being performed. However, in this case, the driver cannot determine whether or not the calibration has been performed. Additionally, the driver cannot recognize accuracy of a current gaze detection result. Thus, the driver cannot determine whether or not a result of detection of the gaze detection apparatus is normal. The driver may have a feeling of anxiety, a feeling of discomfort, and a feeling of distrust toward a result of detection by a gaze detection apparatus.

For example, when a driver of a vehicle equipped with a gaze detection apparatus is changed into a new driver, a warning sound for the inattentive driving may be frequently outputted although the new driver looks in a front direction. In this case, the new driver cannot determine whether a cause of the frequent output of the warning sound is lack of calibration corresponding to the new driver or malfunction of the gaze detection apparatus. As a result, the driver may have the above-described feeling of anxiety and the like.

According to the technique described in Patent Document 4, although the driver can be aware of whether or not calibration has been performed, the driver can not recognize accuracy of a current gaze detection result.

Accordingly, the driver may have the above-described feeling of anxiety and the like.

SUMMARY

In view of the foregoing, it is an objective of the present disclosure to provide a technique that can facilitate confirmation of gaze detection accuracy.

According to a first example of the present disclosure, a gaze detection apparatus is provided. The gaze detection apparatus includes: a gaze detection section that detects gaze of a target person; a display section that includes a display screen for displaying an image; a first gaze position determination section that operates to determine, based on a result of detection by the gaze detection section, whether or not the display screen lies in the gaze of the target person; and a first display control section that operates to display a first detection result image at an intersection point between the gaze of the target person and the display screen when the first gaze position determination section determines that the display screen lies in the gaze of the target person. The first detection result image is a preset image and indicates the result of detection of the target person's gaze.

According to a second example of the present disclosure, a gaze detection method is provided. The gaze detection method includes: detecting gaze of a target person; determining, based on a result of the detecting of the gaze of the target person, whether or not a display screen of a display section for displaying an image lies in the gaze of the target person; and displaying a first detection result image at an intersection point between the gaze of the target person and the display screen when it is determined that the display screen lies in the gaze of the target person. The first detection result image is a preset image and indicates the result of the detecting of the gaze of the target person.

The above gaze detection apparatus and method can facilitate confirmation of gaze detection accuracy.

BRIEF DESCRIPTION OF THE DRAWINGS

The above and other objects, features and advantages of the present disclosure will become more apparent from the following detailed description made with reference to the accompanying drawings. In the drawings.

DETAILED DESCRIPTION

First Embodiment

Figure 1:
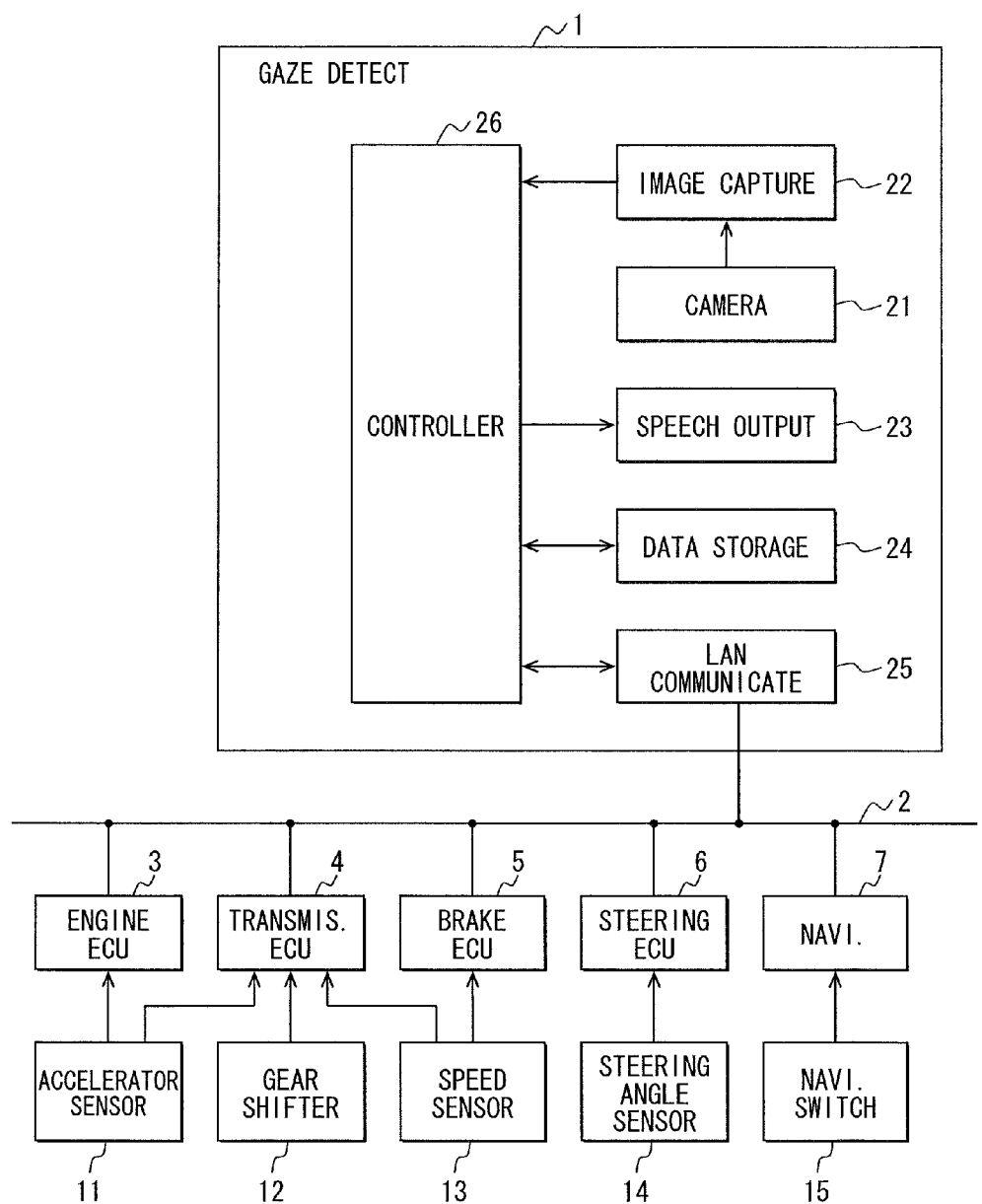
FIG. 1 is a block diagram illustrating a gaze detection apparatus and an in-vehicle LAN.

A first Embodiment will be described with reference to the accompanying drawings. FIG. 1 is a block diagram illustrating a gaze detection apparatus 1 and an in-vehicle LAN 2 of the first embodiment. The gaze detection apparatus 1 is connected with the in-vehicle LAN 2.

As shown in FIG. 1, the gaze detection apparatus 1 is mounted to a vehicle, and is connected with various electronic control units (ECUs) and in-vehicle apparatuses via the in-vehicle LAN 2. The various ECUs include an engine ECU 3, a transmission ECU 4, a brake ECU 5, and a steering ECU 6. The in-vehicle apparatus includes a navigation apparatus 7.

The engine ECU 3 controls engine revolution based on at least a detection signal from an accelerator position sensor 11. The accelerator position sensor 11 detects an accelerator position based on an amount of driver's operation of an accelerator pedal.

The transmission ECU 4 performs control or the like to change a transmission gear ratio of an automatic transmission (not shown) in accordance with a driving state of the vehicle based on at least a detection signal from a gear shifter switch 12, the accelerator position sensor 11 or a vehicle speed sensor 13. The gear shifter switch 12 detects position (P, R, N, D, 1st, 2nd etc.) of a gear shifter (not shown) operated by the driver. The vehicle speed sensor 13 detects vehicle speed.

The brake ECU 5 performs antilock brake system (ABS) control, traction control, or the like based on at least a detection signal from a master cylinder pressure sensor (not shown) or the vehicle speed sensor 13. The master cylinder pressure sensor detects an amount of brake pedal operation based on oil pressure of a master cylinder, which compresses and transports brake oil in response to a driver's operation of the brake pedal.

The steering ECU 6 performs power steering control and generates an assist force to assist a change in steering angle of a steering wheel, based on at least a detection signal from a steering angle sensor 14. The steering angle sensor 14 detects a steering angle of a front tire wheel when the driver steers the vehicle.

Figure 3:
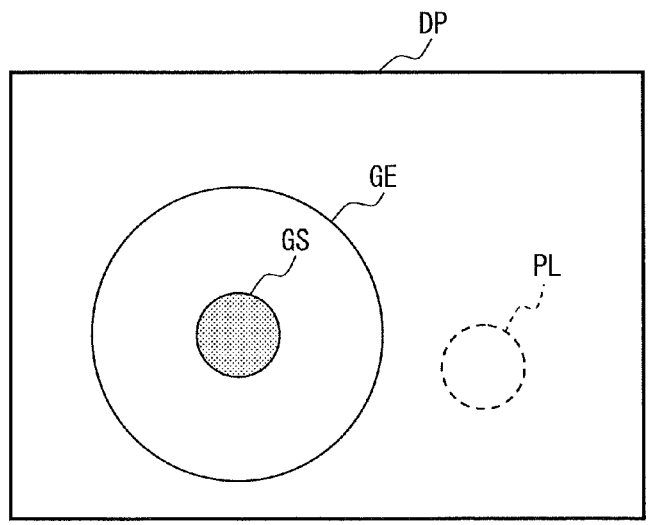
FIG. 3 is a diagram illustrating display of a gaze detection result of the first embodiment.

The navigation apparatus 7 performs, for example, the following control operations. The navigation apparatus 7 receives a GPS signal via a GPS antenna (not shown) to detect a present location of the vehicle based on the GPS signal. The navigation apparatus 7 performs route guidance from a present location to a destination. A navigation switch 15 is arranged in a periphery of a display screen DP (see FIG. 3). Based on a signal from the navigation switch 15 operated by the driver, the navigation apparatus 7 switches image display. The navigation switch 15 includes a present location switch (not shown), a zoom-in/zoom-out switch (not shown), and the like. The present location switch is operated to display the present location of the vehicle. The zoom-in/zoom-out switch is operated to zoom in or zoom out a map display.

A variety of vehicle information (e.g., accelerator position, gear shifter position, vehicle speed, steering angle, and the like) detected with the ECUs 3 to 6, the navigation apparatus 7 and like can be arbitrarily exchanged among the ECU 3 to 6, the navigation apparatus 7 and like.

The gaze detection apparatus 1 is mounted to the vehicle. As shown in FIG. 1, the gaze detection apparatus 1 includes a camera 21, a capture board 22, a speech output device 23, a data storage device 24, an in-vehicle LAN communication device 25, and a controller 26. The camera 21 successively takes an image of a driver seat and its surroundings. The capture board 22 temporarily stores a data of the image taken with the camera 21. The speech output device 23 outputs a variety of guidance speech. The data storage device 24 stores a variety of data. The in-vehicle LAN communication device 25 exchanges a variety of vehicle information with other apparatuses via the in-vehicle LAN 2. The controller 26 performs various processes in accordance with inputs from the data storage device 24 and the in-vehicle LAN communication device 25, thereby controlling the speech output device 23 and the in-vehicle LAN communication device 25 for example.

Figure 2:
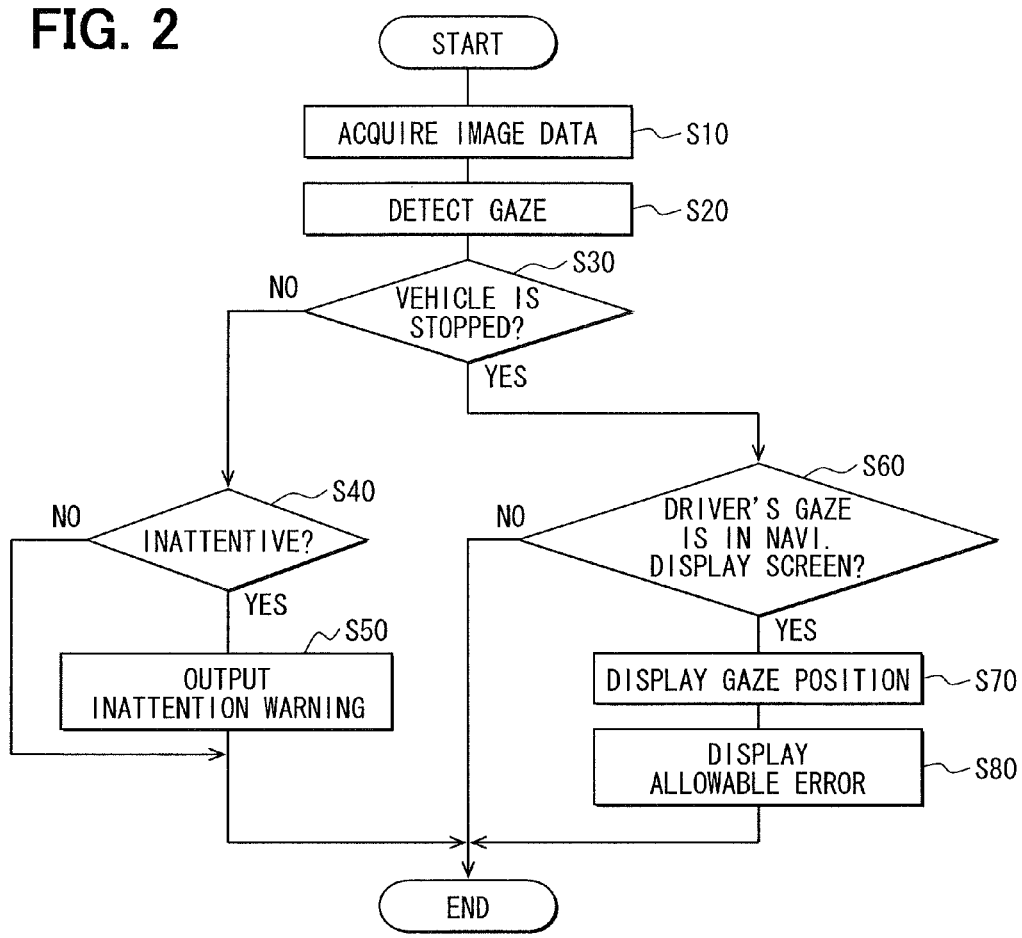
FIG. 2 is a flowchart illustrating an inattention warning process of a first embodiment.

Based on a result of detection of the gaze of the driver, the controller 26 of the gaze detection apparatus 1 performs an inattention warning process for outputting a warning about inattention driving. A procedure of the inattention warning process will be described with reference to FIG. 2. FIG. 2 is a flowchart illustrating the inattention warning process. While the controller 26 is in operation (powered-on), the controller 26 repeatedly performs the inattention warning process.

In the inattention warning process, at S10, the controller 26 causes the camera 21 to take an image and acquires an image data. At S20, the controller 26 detects a direction of eye gaze of the driver by using the image data acquired at S10. In order to detect the gaze of the driver, the present embodiment employs a method described in "Takahiro Ishikawa, Simon Baker, Iain Matthews, and Takeo Kanade, Passive Driver Gaze Tracking with Active Appearance Models, Proceedings of the 11th World Congress on Intelligent Transportation Systems, October, 2004", which is incorporated herein by reference.

At S30, based on a result of detection by the vehicle speed sensor 13, the controller 26 determines whether or not the vehicle equipped with the gaze detection apparatus 1 is stopped. The vehicle equipped with the gaze detection apparatus 1 is also called a subject vehicle or simply called a vehicle. When the vehicle is not stopped, corresponding to NO at S30, the process proceeds to S40. At S40, based on a result of the gaze detection at S20, the controller 26 determines whether or not the driver is inattentive, i.e., whether the driver's driving is inattentive driving. When the driver is not inattentive, corresponding to No at S40, this inattention warning process is ended. When the driver is inattentive, corresponding to YES at S40, the process proceeds to S50. At S50, the controller 26 causes the speech output device 23 to output a speech indicating that the driver is inattentive. After S50, this inattentive driving warning process is ended.

When it is determined at S30 that the vehicle is stopped, corresponding to YES at S30, the process proceeds to S60. At S60, based on the result of the gaze detection, the controller 26 determines whether or not the gaze of the driver is positioned inside the display screen DP (see FIG. 3) of the navigation apparatus. The display screen DP of the navigation apparatus is also referred to as a navigation display screen DP.

When the driver's gaze is not positioned inside the navigation display screen DP, corresponding to NO at S60, this inattention warning process is ended. When the driver's gaze is positioned inside the navigation display screen DP, corresponding to YES at S60, the process proceeds to S70. At S70, the controller 26 displays a gaze position indication image GS on the navigation display screen DP so that the gaze position indication image GS is displayed at a place matching the position of the driver's gaze (see FIG. 3). The gaze position indication image GS is an image indicating the position of the driver's gaze. At S80, the controller 26 displays an allowable error indication image GE (see FIG. 3) on the navigation display screen DP. The allowable error indication image GE indicates a range of an allowable gaze detection error of the gaze detection apparatus 1. After S80, this inattention warning process is ended. In the present embodiment, a circle is set as the allowable error indication image GE. This circle corresponds to a movement distance of the gaze on the navigation display screen DP when an angle of the gaze is changed by 5 degrees with respect to a center of the gaze position indication image GS.

According to the above configuration, the gaze detection apparatus 1 first detects the gaze of the driver (S20), and then determines whether or not the navigation display screen DP lies in the gaze of the driver based on a result of the gaze detection (S60). When the navigation display screen DP lies in the gaze of the driver (YES at S60), the gaze detection apparatus 1 displays the gaze position indication image GS on the navigation display screen DP to indicate the result of detection of the driver's gaze (70) so that the gaze position indication image GS is displayed at an intersection point between the navigation display screen DP and the driver's gaze (line of sight).

Therefore, it is highly likely that when the driver is viewing the navigation display screen DP, a detection result of the driver's gaze is displayed on the navigation display screen DP. When the gaze position indication image GS is displayed when the driver is viewing the navigation display screen DP, the driver can compares the following two places with each other. One is a placed on the display screen at which the driver is actually and presently looking at (see the gaze position PL in FIG. 3). The other is a place on the display screen at which the gaze position indication image GS is displayed. Because of this, the driver can easily confirm detection accuracy of the gaze detection apparatus 1. Therefore, a situation where the driver has a feeling of anxious toward a detection result of the gaze detection apparatus 1 can be prevented from occurring.

Furthermore, the allowable error indication image GE, which indicates an allowable range of a gaze detection error of the gaze detection apparatus 1, is displayed so that its center is at the display position of the gaze position indication image GS (S80). Because of this, the driver can check whether the place on the navigation display window DP at which the driver is actually and presently looking (see the gaze position PL in FIG. 3) is in the allowable range centered at the display position of the gaze position indication image GS. Therefore, the deriver can determine, by himself or herself, that the error of gaze detection is in an allowable range if the actual driver's gaze position is in the allowable range, and the error of gaze detection stands out of the allowable range if the actual driver's gaze position is not in the allowable range.

When the vehicle is stopped (YES at S30), the gaze detection apparatus 1 performs control to display the result of the gaze detection on the navigation display screen DP (S70). Because of this, the driver can check the result of the gaze detection in a state in which the driver is safe even when gazing at the navigation display screen DP.

In the present embodiment, the controller 26 performing S20 is an example of a gaze detection means, process or section. The navigation display screen DP is an example of a display screen. The navigation apparatus 7 is an example of a display means or section. The controller 26 performing S60 is an example of a first gaze position determination means, process or section. The controller 26 performing S70 and/or S80 is an example of a first display control means, process and section. The gaze position indication image GS is an example of a first detection result image. The controller 26 performing S30 is an example of a third prohibition means, process or section.

Second Embodiment

A second Embodiment will be described with reference to the accompanying drawings. Explanation on a difference from the first embodiment will be given.

Figure 4:
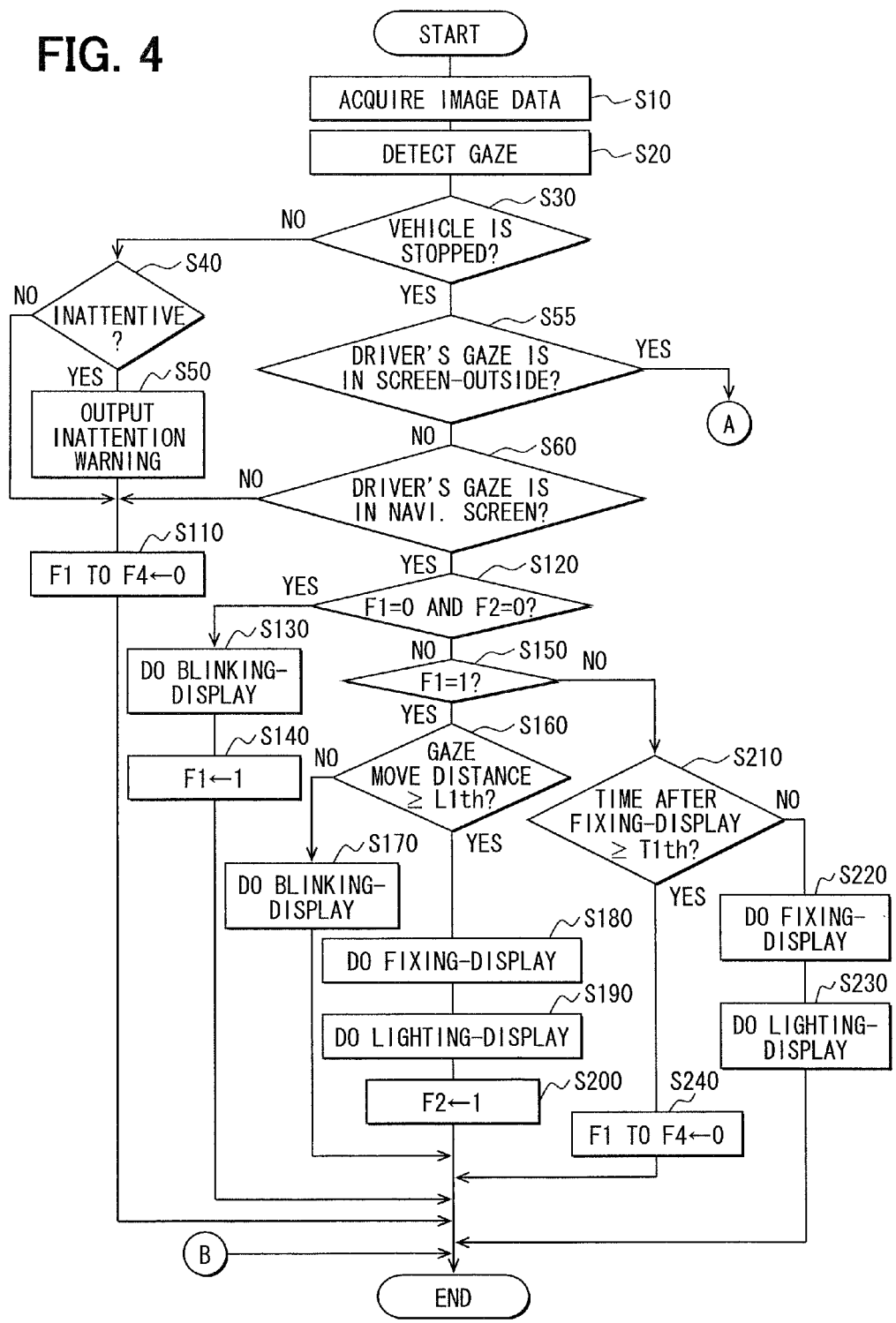
FIG. 4 is a flowchart illustrating a first half of an inattention warning process of a second embodiment.
Figure 5:
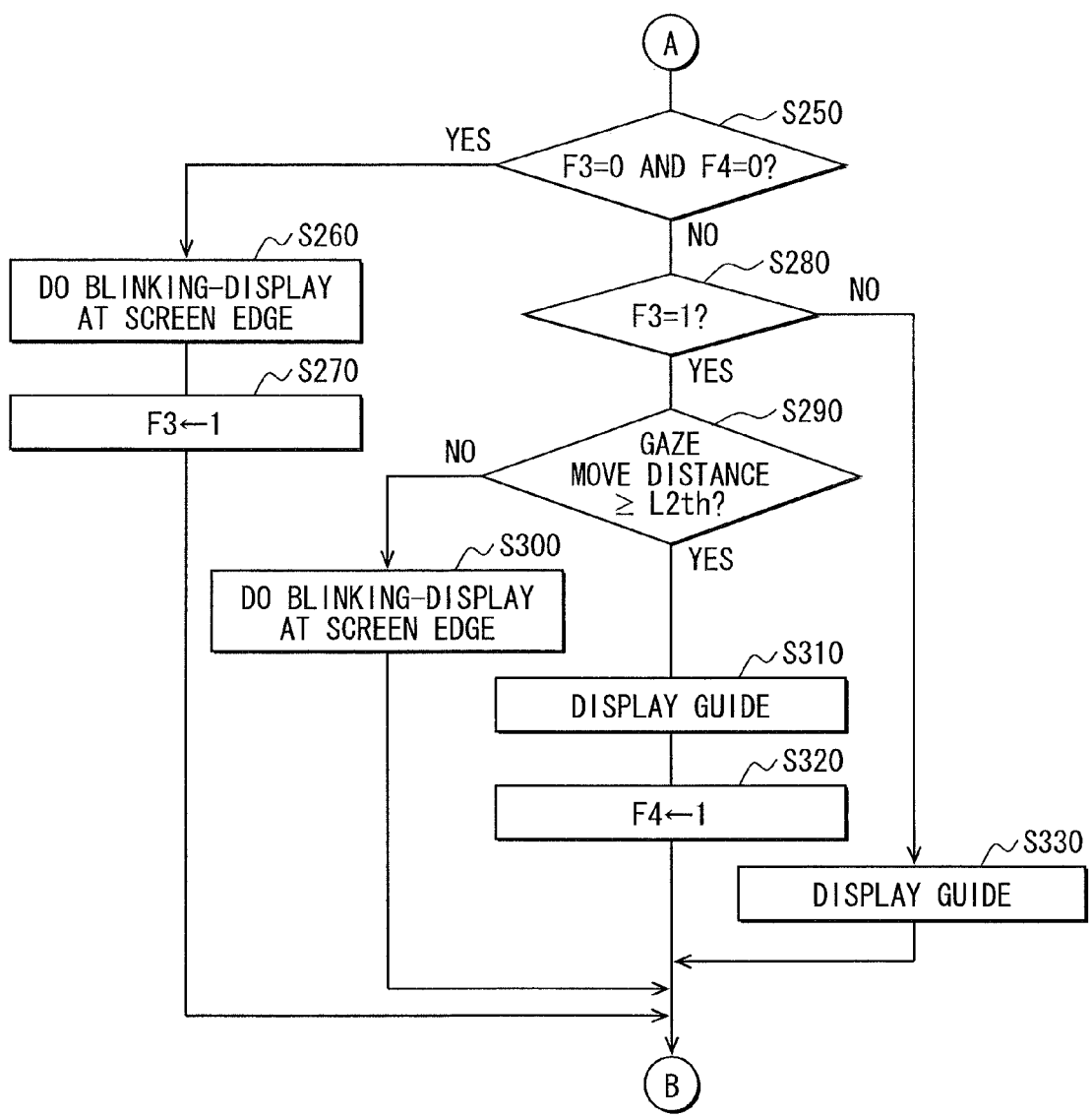
FIG. 5 is a flowchart illustrating a latter half of the inattention warning process of the second embodiment.

The gaze detection apparatus 1 of the second embodiment can be substantially the same as that of the first embodiment, except that the inattention warning process is changed. The inattention warning process of the second embodiment will be described with reference to FIGS. 4 and 5. FIG. 4 illustrates a first half of the inattention warning process of the second embodiment. FIG. 5 illustrates a latter half of the inattention warning process.

As shown in FIGS. 4 and 5, the inattention driving warning process of the second embodiment differs from that of the first embodiment in that steps S70 to S80 are omitted and that steps S55 and S110 to S330 are added.

More specifically, when the step S50 is completed or when it is determined at S60 that the driver's gaze is not positioned inside the navigation display screen DP (NO at S60), the process proceeds to S110. At S110, the controller 26 clears a blinking display flag F1, a fixing display flag F2, a screen edge display flag F3, and a guidance display flag F4. After S110, this inattention warning process is ended. In the following description, setting a flag means making value of the flag "1". Clearing a flag means making a value of the flag "0".

Figure 6:
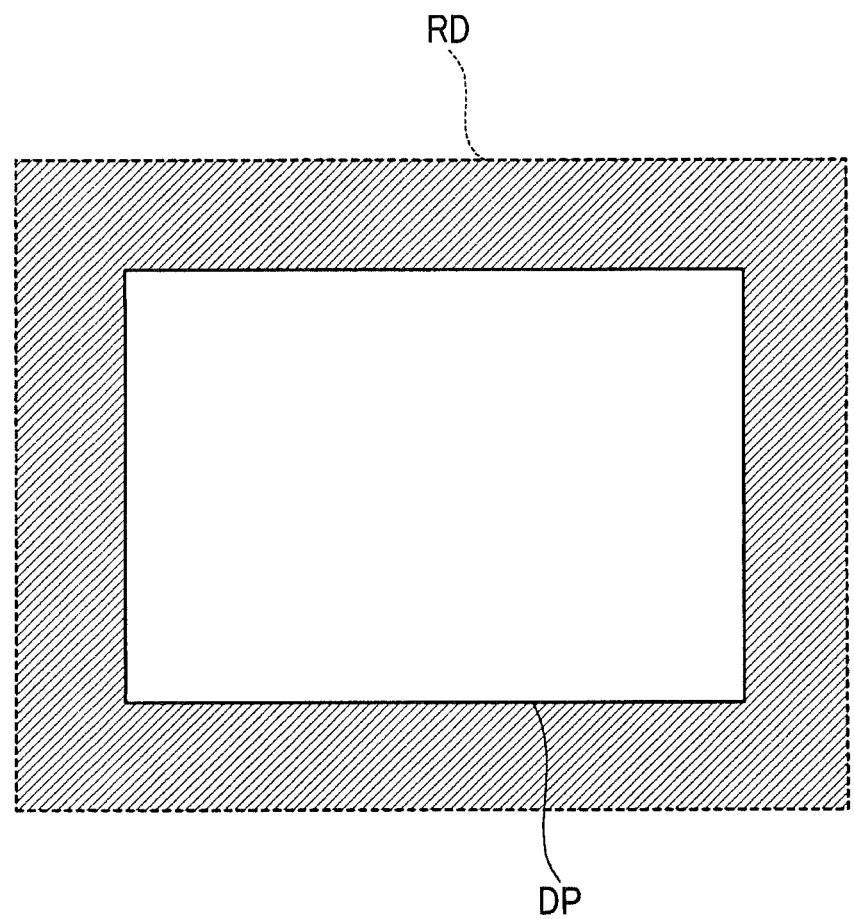
FIG. 6 is a diagram illustrating a screen-outside displayable region.

When it is determined at S30 that the vehicle is stopped, corresponding to YES at S30, the process proceeds to S55. At S55, the controller 26 determines whether or not the driver's gaze is positioned inside a screen-outside displayable region RD. The screen-outside displayable region RD is a preset region (see FIG. 6), which surrounds the navigation display screen DP and which is on the same plane as the navigation display screen DP.

When the driver's gaze is not positioned inside the screen-outside displayable region RD, corresponding to NO at S55, the process proceeds to S60. When it is determined at S60 that the driver's gaze is positioned inside the navigation display screen DP, corresponding to YES at S60, the process proceeds to S120. At S120, the controller 26 determines whether or not both of the blinking display flag F1 and the fixing display flag F2 are cleared. When both of the blinking display flag F1 and the fixing display flag F2 are cleared, corresponding to YES at S120, the process proceeds to S130. At S130, the controller 26 displays the gaze position indication image GS on the navigation display screen DP, such that the gaze position indication image GS is at the place matching the position of the driver's gaze on the navigation display screen DP, and that the gaze position indication image GS is blinking in, for example, green color. That is, the blinking display of the gaze position indication image GS at the above place is performed at S130. At S140, the controller 26 sets the blinking display flag F1 and clears flags F2, F3, F4 other than the blinking display flag F1. After S140, this inattentive driving warning process is ended.

When any one of the blinking display flag F1 and the fixing display flag F2 is set, corresponding to NO at S120, the process proceeds to S150. At S150, the controller 26 determines whether or not the blinking display flag F1 is set. When the blinking display flag F1 is set, corresponding to YES at S150, the process proceeds to S160. At S160, the controller 26 determines whether or not the gaze has moved by a preset fixing display determination distance L1th or more on the navigation display screen DP since the blinking display of the gaze position indication image GS was started at S130. In the present embodiment, the fixing display determination distance L1th is set to a movement distance that corresponds to an angle (about 2 degrees) of center vision field of human being.

Figure 7A:
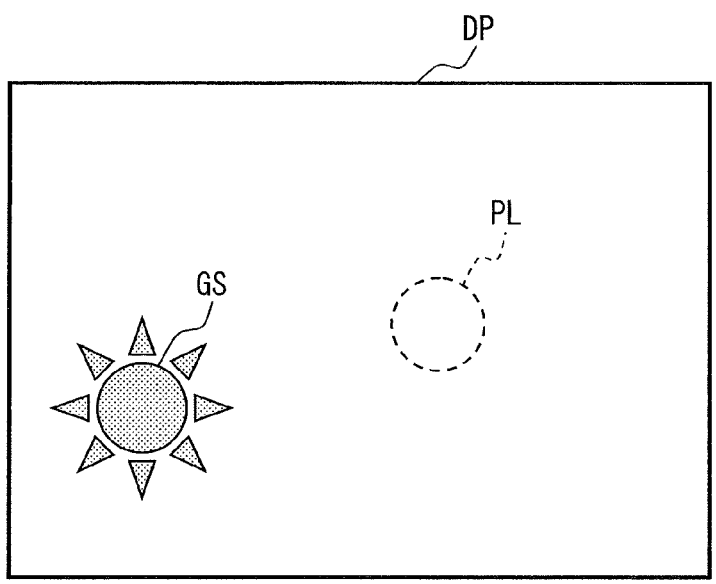
FIGS. 7A and 7B are diagrams each illustrating display of a gaze detection result of the second embodiment.
Figure 7B:
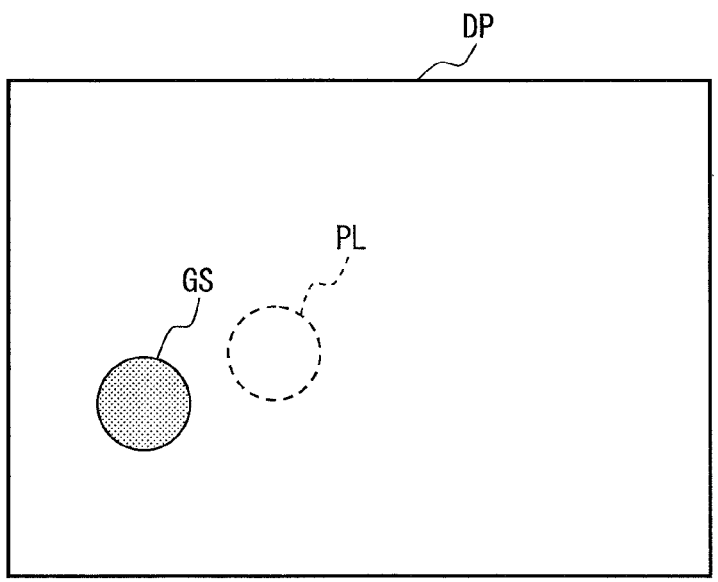

When the movement distance of the gaze is smaller than the fixing display determination distance L1th, corresponding to NO at S160, the process proceeds to S170. At S170, the controller 26 displays the gaze position indication image GS by blinking it in a manner similar to that at S130. That is, the blinking display of the gaze position indication image GS is performed at S170. When the movement distance of the gaze is greater than or equal to the fixing display determination distance L1th, corresponding to YES at S160, the process proceeds to S180. At S180, the controller 26 fixedly displays the gaze position indication image GS in such way that the gaze position indication image GS is fixed at its present display position (see FIG. 7B). That is, the fixing display of the gaze position indication image GS is performed at S180. At S190, the controller 26 causes the fixed gaze position indication image GS to be lighting (not blinking) in green color. That is, the lighting display of the gaze position indication image GS is performed at S190. At S200, the controller 26 sets the fix display flag F2, and clears the flags F1, F2, F4 other than the fix display flag F2. After S200, this inattention warning process is ended.

When it is determined at S150 that the blinking display flag F1 is cleared, corresponding to NO at S150, it is determined that the fixing display flag F2 is set. In this case, the process proceeds to S210. At S210, the controller 26 determines whether or not a preset fix release determination time T1th has elapsed since the fixing display of the gaze position indication image GS was started at S180. When the fix release determination time T1th has not elapsed, corresponding to NO at S210, the process proceeds to S220. At S220, the controller 26 fixedly displays the gaze position indication image GS in a manner similar to that at S180. That is, the fixing display of the gaze position indication image GS is performed at S220. At S230, the controller 26 displays the gaze position indication image GS by blinking it in a manner similar to that at S190. That is, the blinking display of the gaze position indication image GS is performed at S230. After S230, the inattention warning process is ended.

When the fix release determination time T1th has elapsed from the start of the fixing display, corresponding to YES at S210, the process proceeds to S240. At S240, the controller 26 clears the blinking display flag F1, the fixing display flag F2, the screen edge display flag F3, and the guidance display flag F4. After S240, the inattention warning process is ended.

Figure 8A:
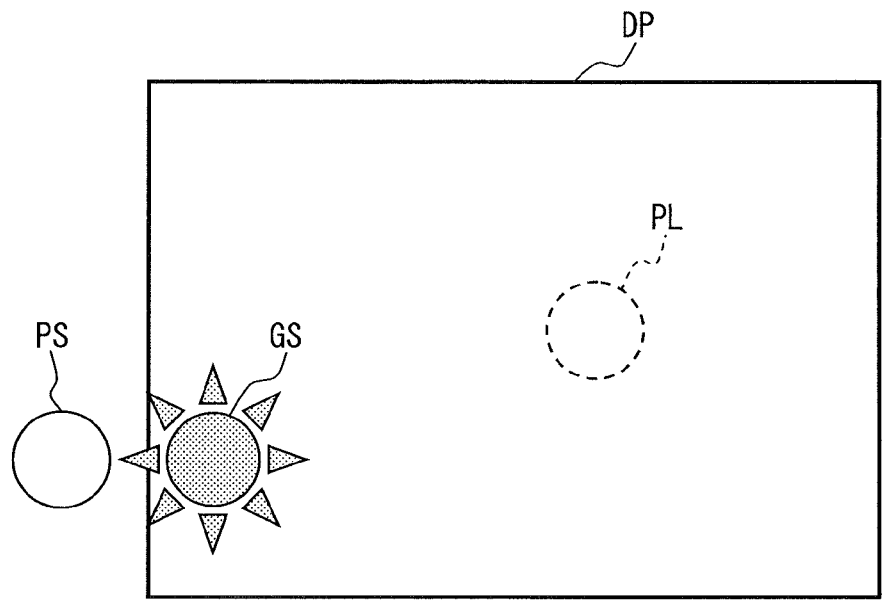
FIGS. 8A and 8B are diagrams each illustrating a gaze guidance display of the second embodiment.

When it is determined at S55 that the driver's gaze is positioned inside the screen-outside displayable region RD, corresponding to YES at S55, the process proceeds to S250. At S250, the controller 26 determines whether or not both of the screen edge display flag F3 and the guidance display flag F4 are cleared. When both of the screen edge display flag F3 and the guidance display flag F4 are cleared, corresponding to YES at S250, the process proceeds to S260. At S260, the controller 26 performs the blinking display of the gaze position indication image GS in red color, so that the gaze position indication image GS is at a particular place on the navigation display screen DP. The particular place is a place that is closest to the position of the driver's gaze on the screen-outside displayable region RD (see the gaze position PS in FIG. 8A). Thus, the particular place is on the outer edge of the navigation display screen DP. At S270, the controller 26 sets the screen edge display flag F3 and clears other flags F1, F2, F4. After S270, this inattention warning process is ended.

When any one of the screen edge display flag F3 and the guidance display flag F4 is set, corresponding to NO at S250, the process proceeds to S280. At S280, the controller 26 determines whether or not the screen edge display flag F3 is set. When the screen edge display flag F3 is set, corresponding to YES at S280, the process proceeds to S290. At S290, the controller 26 determines whether or not the gaze has moved by a preset guidance display determination distance L2th or more on the navigation display screen DP since the blinking display of the gaze position indication image GS was started at S260. In the present embodiment, the guidance display determination distance L2th is set to a movement distance that corresponds to an angle (about 2 degrees) of center vision field of human being.

Figure 8B:
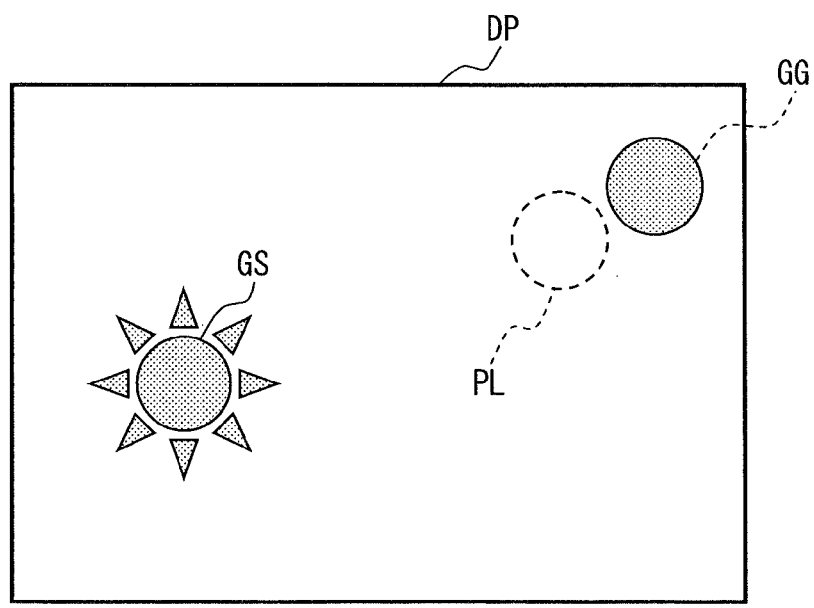

When the movement distance of the gaze is smaller than the guidance display determination distance L2th, corresponding to NO at S290, the process proceeds to S300. At S300, the controller 26 performs the blinking display of the gaze position indication image GS in a manner similar to that at S260. When the movement distance of the gaze is greater than or equal to the guidance display determination distance L2th, corresponding to YES at S290, the process proceeds to S310. At S310, the controller 26 displays a gaze guidance image GG (see FIG. 8B) in blue color so that the gaze guidance image GG is lighting (not blinking). That is, the lighting display of the gaze guidance image GG is performed at S310. A display position of the gaze guidance image GG is on an opposite side of the gaze position indication image GS, which was displayed at S260, from the display outside displayable region RD. At S320, the controller 26 sets the guidance display flag F4 and clears the other flags F1, F2, F3. After S320, this inattentive driving warning process is ended.

When it is determined at S280 that the screen edge display flag F3 is cleared, it is determined that the guidance display flag F4 is set. In this case, the process proceeds to S330. At S330, the controller 26 performs the lighting display of the gaze guidance image GG in a manner similar to that at S310. Thereafter, the inattention warning process is ended.

According to the above configuration, the gaze detection apparatus 1 detects the driver's gaze (S20), and then determines, based on a result of the gaze detection, whether or not the navigation display screen DP lies in the driver's gaze (S60). When the navigation display window DP lies in the driver's gaze (YES at S60), the gaze detection apparatus 1 performs the blinking display of the gaze position indication image GS at a place where the driver's gaze intersects with the navigation display screen DP (S130). The gaze position indication image GS indicates the result of the driver's gaze detection. Thereafter, based on the result of the gaze detection, the gaze detection apparatus 1 determines whether or not the drive's gaze is moved (S160). When the drive's gaze is moved (YES at S160), the blinking display of the gaze position indication image GS is terminated (S200, S150).

Furthermore, when the gaze detection apparatus 1 displays the gaze position indication image GS while the driver is viewing the navigation display screen DP, the driver typically moves his or her gaze to take a look at this gaze position indication image GS. Thus, it can be determined that the movement of the gaze after the display of the gaze position indication image GS is a response to the display of the gaze position indication image GS. Because of this, it is possible to prevent an occurrence of the following situation. After the driver has recognized the blinking gaze position indication image GS, the blinking gaze position indication image GS wastefully continues to be displayed on the navigation display screen DP.

When the driver's gazes is moved (YES at S160), the lighting display of the gaze position indication image GS is performed so that the gaze position indication image GS is lighting at place where the driver's gaze intersects with the navigation display screen DP at the time of the movement of the driver's gaze (S180, S190).

Specifically, when the driver starts moving his or her gaze to check the gaze position indication image GS, the display position of the gaze position indication image GS is fixed. Because of this, it is possible to prevent an occurrence of the following situation. When the driver tries to check the gaze position indication image GS by moving his or her gaze, the gaze position indication image GS moves accordingly, and as a result, the driver cannot look fixedly at the gaze position indication image GS. Therefore, in the central vision field, the driver can surely check the display position of the gaze position indication image GS.

Furthermore, when the fix release determination time T1th has elapsed since the fixing display of the gaze position indication image GS was started (YES at S210), the fixing display of the gaze position indication image GS is terminated (S240, S120). Because of this, it is possible to prevent an occurrence of the following situation. After the driver has recognized the fixing display of the gaze position indication image GS, the fixing display of the gaze position indication image GS on the navigation display screen DP wastefully continues.

Furthermore, when the fix release determination time T1th has elapsed since the fixing display of the gaze position indication image GS was started (YES at S210), control is performed to perform the blinking display of the gaze position indication image GS (S240, S120, S130) if the navigation display screen DP lies in the driver's gaze. Because of this, the driver can reconfirm the accuracy of the gaze detection apparatus 1 at a different time point.

Furthermore, the blinking display of the gaze position indication image GS is a form of display that changes over time. Thus, even if the gaze position indication image GS is displayed at a place in the driver's peripheral vision field, the driver can notice the gaze position indication image GS more easily as compared with a case where the gaze position indication image GS is displayed in a form that does not change over time.

Furthermore, in response to the movement of the driver's gaze after the blinking display of the gaze position indication image GS, the gaze position indication image GS becomes lighting (lighting display). That is, there is a change in display form between before and after the movement of the driver's gaze. Because of this, from the display form of the gaze position indication image GS, the driver can determine whether the currently-displayed gaze position indication image GS is a movable image or a fixed image. In the above, the movable image is movable in response to the movement of the driver's gaze. The fixed image is fixedly displayed and is not moved in response to the movement of the driver's gaze.

Furthermore, based on a result of the gaze detection, the gaze detection apparatus 1 determines (S55) whether or not the screen-outside displayable region RD, which is preset so as to surround the navigation display screen DP, lies in the driver's gaze. When the screen-outside displayable region RD lies in the driver's gaze (YES at S55), the blinking display of the gaze position indication image GS is performed (S260). Specifically, the gaze position indication image GS blinks in, for example, red color, and is located at a particular place on the outer edge of the navigation display screen DP. In the above, the particular place is set to a place closest to an intersection point between the driver's gaze and the screen-outside displayable region RD. After the gaze position indication image GS is displayed to blink in red color, the gaze guidance image GG is displayed inside the navigation display screen DP so that the gaze guidance image GG is located on an opposite side of the gaze position indication image GS from the screen-outside displayable region RD (S310). Since the gaze guidance image GG is displayed on an opposite side of the gaze position indication image GS from the screen0outside displayable region RD, when the driver starts to look at the gaze guidance image GG, the driver's gaze moves toward an inside of the navigation display screen DP.

Because of this, an image indicating a gaze position based on a result of gaze detection can be displayed on the navigation display screen DP. Accordingly, the driver can compare (i) the position on the display screen at which he or she is actually looking at the present time and (ii) the gaze position on the navigation display screen which is based on the result of gaze detection.

In the present embodiment, the controller 26 performing S160 is an example of a first gaze movement detection means, process and section. The controller 26 performing S150 and S200 is an example of a first prohibition means, process and section. The controller 26 performing S180 and S190 is an example of a second display control means, process and section. The controller 26 performing S120, S210 and S240 is an example of a second prohibition means, process and section. The controller 26 performing S120, S210 and S240 is also an example of a first release means, process and section. The gaze position indication image GS that is blinking in green color is an example of a first detection result image. The gaze position indication image GS that is lighting in green color is an example of a second detection result image. The fix release determination time T1th is an example of a display termination determination time.

The controller 26 performing S55 is an example of a second gaze position determination means, process and section. The controller 26 performing S260 is an example of a third display control means, process and section. The controller 26 performing S310 is an example of a guidance display control means, process and section. The gaze position indication image GS blinking in red color is an example of a third detection result image. The gaze guidance image GG is an example of an image for guidance or a guidance image.

Third Embodiment

A third embodiment will be described with reference to the accompanying drawings. Explanation on a difference from the first embodiment will be given.

A gaze detection apparatus 1 of the third embodiment can be substantially the same as that of the first embodiment except the following points. In the third embodiment, the gaze detection apparatus 1 further includes a gaze detection display switch (not shown), which is operated to display a result of gaze detection is added. Additionally, the inattention warning process is modified.

Figure 9:
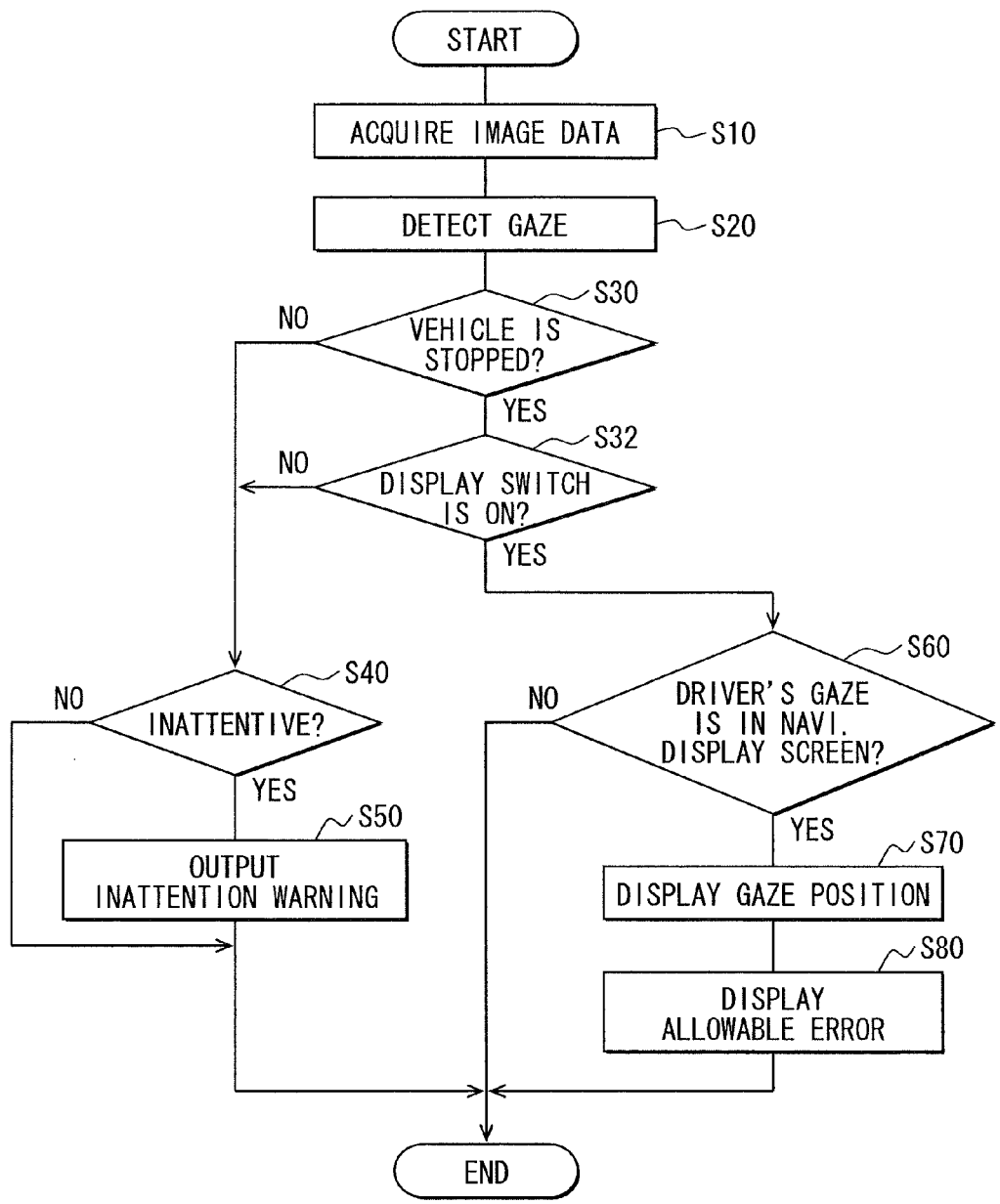
FIG. 9 is a flowchart illustrating an inattention warning process of a third embodiment.

The inattention warning process of the third embodiment will be described with reference to FIG. 9. FIG. 9 is a flowchart illustrating the inattention warning process of the third embodiment. As shown in FIG. 9, a difference in the inattention warning process between the first and third embodiments is that S32 is added to the third embodiment.

More specifically, when it is determined at S30 that the vehicle is stopped, corresponding to YES at S30, the process proceeds to S32. At S32, the controller 26 determines whether or not the gaze detection display switch is on. When the gaze detection display switch is on, corresponding to YES at S32, the process proceeds to S60. When the gaze detection display switch is off, corresponding to NO at S32, the process proceeds to S40.

According to the above configuration, when the gaze detection display switch is tuned off (NO at S32), the control for displaying a result of gaze detection is prohibited from being performed. As a result, it is possible to prevent an occurrence of the following situation. Even when a user of the gaze detection apparatus 1 (e.g., the driver) thinks that confirmation of the result of gaze detection is unnecessary, a result of gaze detection is displayed, and accordingly, the user has a feeling of discomfort.

In the present embodiment, the controller 26 performing S32 is an example of a fourth prohibition means, process or section.

Fourth Embodiment

A fourth embodiment will be described with reference to the accompanying drawings.

Explanation on a difference from the first embodiment will be given.

Figure 10:
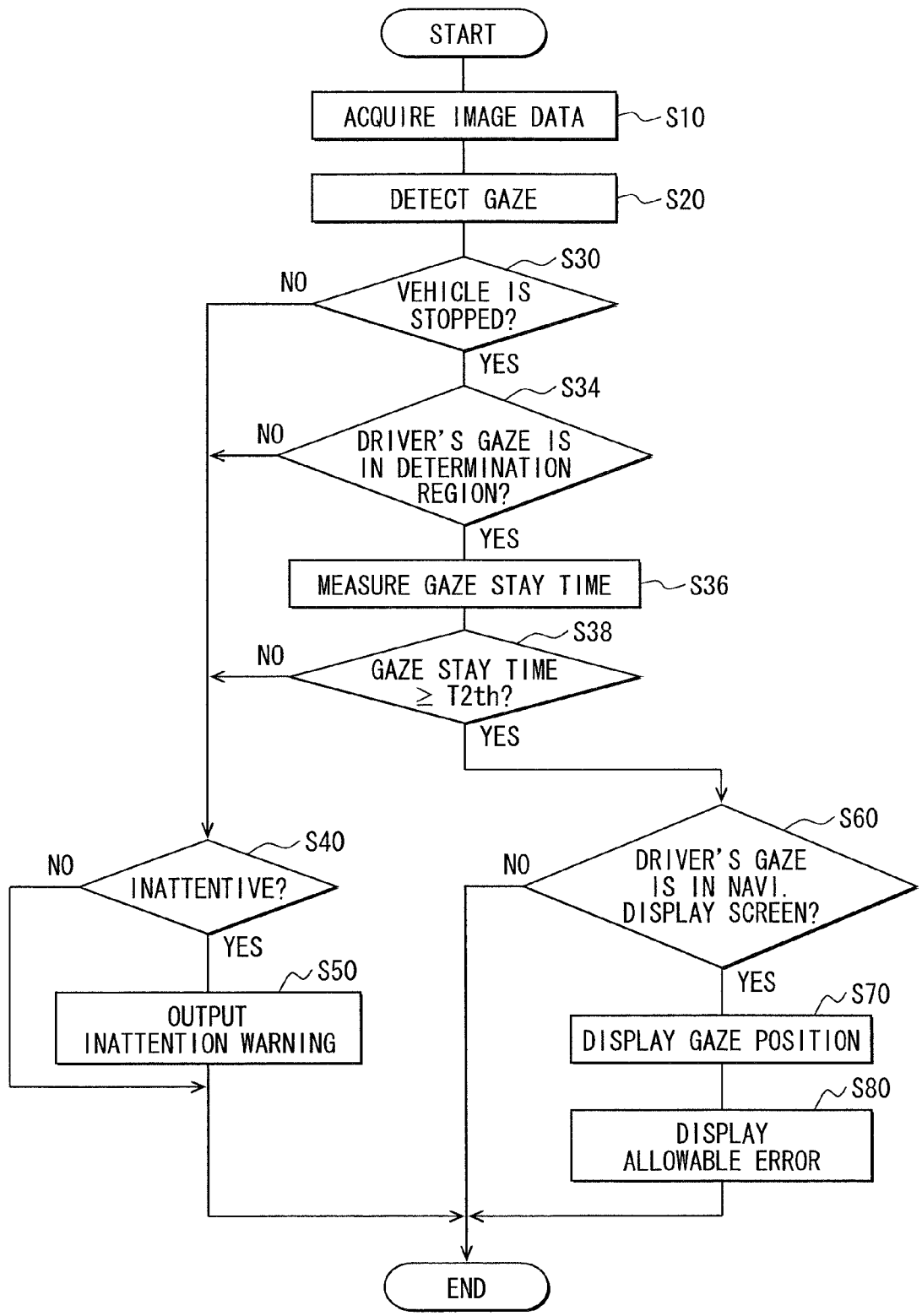
FIG. 10 is a flowchart illustrating an inattention warning process of a fourth embodiment.

The gaze detection apparatus 1 of the fourth embodiment can be substantially the same as that of the first embodiment, expect that the inattention warning process is changed. The inattention warning process of the fourth embodiment will be described with reference to FIG. 10. FIG. 10 is a flowchart illustrating the inattention warning process of the fourth embodiment.

Figure 11:
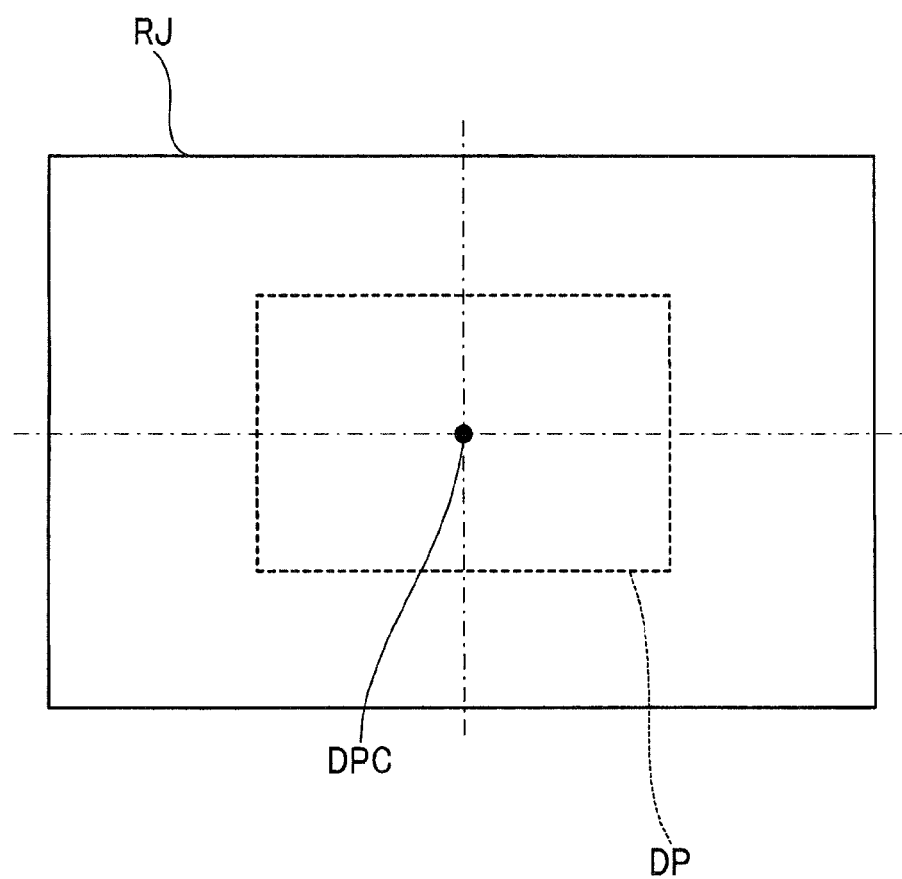
FIG. 11 is a diagram illustrating a display determination region.

As shown in FIG. 10, a difference in the inattention warning process between the first and fourth embodiments is that S34, S36 and S38 are added to the third embodiment. Specifically, when it is determined at S30 that the vehicle is stopped, corresponding to YES at S30, the process proceeds to S34. At S34, the controller 26 determines whether or not the driver's gaze lies in a display determination region RJ. The display determination region RJ is, as shown in FIG. 11, a preset region containing the navigation display screen DP and a surrounding of the navigation display screen DP. The display determination region RJ and the display determination region RJ are on the same plane. In the present embodiment, in consideration of an error of gaze detection of the gaze detection apparatus 1, the display determination region RJ is set to such a rectangular region that: the center of the display determination region RJ is at a center DPC of the navigation display screen DP; and the area of the display determination region RJ is four times as large as the navigation display screen DP.

When the driver's gaze does not lie in the display determination region RJ, corresponding to NO at S34, the process proceeds to S40. When the driver's gaze lies in the display determination region RJ, corresponding to YES at S34, the process proceeds to S36. At S36, the controller 26 measures a time in which the driver's gaze keeps staying in the display determination region RJ. This measured time is also called herein a gaze stay time.

Thereafter, at S38, the controller 26 determines whether or not the gaze stay time is greater than or equal to a preset result display determination time T2th. When the gaze stay time is less than the result display determination time T2th, corresponding to NO at S38, the process proceeds to S40. When the gaze stay time is greater than or equal to the result display determination time T2th, corresponding to YES at S38, the process proceeds to S60.

According to the above configuration, based on a result of gaze detection, the gaze detection apparatus 1 performs measurement of the gaze stay time (S34, S36). The gaze stay time is a time in which the driver's gaze stays in the display determination region RJ, which is a preset region containing the navigation display screen DP. When the gaze stay time is greater than or equal to the result display determination time T2th (YES at S38), the gaze detection apparatus 1 performs control to display the result of gaze detection on the navigation display screen DP (S70).

Because of this, when the driver would like to check a result of gaze detection, the driver can instruct, by performing a simple operation without turning on the gaze detection switch of the third embodiment, the gaze detection apparatus 1 to display the result of gaze detection on the navigation display screen D. For example, by fixedly looking at an inside of the display determination region RJ, the driver can instruct the gaze detection apparatus 1 to display the result of gaze detection on the navigation display screen D.

In the present embodiment, the controller 26 performing S34 and S36 is an example of a stay time measurement means, process or section. The controller performing S38 is an example of a fifth prohibition means, process or section. The result display determination time T2th is an example of a determination prohibition time.

Embodiments are not limited to the above-described embodiment, and can have various forms.

For example, in the above embodiments, the stopping of the vehicle is used as a condition for displaying a result of gaze detection on the navigation display screen DP. However, this does not limit the condition. For example, when an ignition (IG) switch is turned on, or when the vehicle is ready to start, a result of gaze detection may be displayed on the navigation display screen DP. Additionally, whether or not a parking brake is on or off may be added to the above condition for displaying a result of gaze detection.

The first embodiment displays the allowable error indication image GE to enable the driver to determine whether or not a result of gaze detection is in the allowable error range. In this relation, it is considered that, when the driver is operating the navigation switch 15 for example, the diver is fixedly looking at the navigation switch 15. In view of this, the gaze detection apparatus 1 may compare a position of the navigation switch 15 with the gaze position, which is based on a detection result of the gaze of the driver who is operating the navigation switch 15. Based on this comparison, the gaze detection apparatus 1 may determine whether or not the result of gaze detection is in the allowable error range. When the gaze detection apparatus 1 determines that the result of gaze detection is not in the allowable error range, the gaze detection apparatus 1 may notify the driver of this result of determination.

In the first embodiment, the allowable error indication image GE indicative of an allowable range of gaze detection error of the gaze detection apparatus 1 is displayed so that the center of the allowable error indication image GE matches the center of the gaze position indication image GS. In the second embodiment, the allowable error indication image GE may be displayed so that the center of the allowable error indication image GE matches the center of the blinking gaze position indication image GS or the lighting gaze position indication image GS.

In the second embodiment, the gaze guidance image GG is displayed to guide the driver's gaze toward the navigation display screen DP. However, although the driver's gaze is moved after the display of the gaze guidance image GG, the driver's gaze may not be positioned inside the navigation display screen DP. In this case, the gaze detection apparatus 1 may notify the driver that the calibration of gaze detection is needed, or that an error of gaze detection is large.

The gaze detection apparatus 1 may be configured to perform the calibration of gaze detection in response to a predetermined driver's operation, e.g., a driver's operation on the navigation switch 15. In the above embodiments, a detection result of the driver's gaze is displayed on the navigation display screen DP. Alternatively, a gaze detection result may be displayed on, for example, a multi-display in a meter (e.g., instrumental panel), a head-up display (HUB) or the like.

Alternatively, a gaze detection result may be displayable on multiple display screens, so that in accordance with orientation of driver's face, the gaze detection apparatus selects a display screen that displays the gaze detection result. In the above embodiments, the blinking display is illustrated as one display form of the gaze position indication image GS. Alternatively, the display form of the gaze position indication image GS may change in color, shape or size over time. Further, the display form of the gaze position indication image GS may be a combination of a color change, a shape change and/or a size change.

Furthermore, the gaze detection apparatus 1 may enable the driver to select the display form of the gaze position indication image GS.

The present disclosure has various aspects. For example, according to a first aspect, a gaze detection apparatus includes a gaze detection section, a display section, a first gaze position determination section, and a first display control section. The gaze detection section detects gaze of a target person. The display section includes a display screen for displaying an image. The first gaze position determination section operates to determine, based on a result of detection by the gaze detection section, whether or not the display screen lies in the gaze of the target person. When the first gaze position determination section determines that the display screen lies in the gaze of the target person, the first display control section operates to display a first detection result image at an intersection point between the gaze of the target person and the display screen. The first detection result image is a preset image and indicates the result of detection of the target person's gaze.

According to the above gaze detection apparatus, when it is determined, based on the result of detection by the gaze detection section, that the target person is viewing the display screen, the first detection result image is displayed at a position of the target person's gaze on the display screen. Thus, it is highly likely that when the target person is viewing the display screen, the result of detection of the target person's gaze is displayed on the display screen. When the first detection result image is displayed while the target person is viewing the display screen, the target person can compare (i) a position on the display screen at which the target person is presently actually looking and (ii) a display position of the first detection result image on the display screen. Thus, the target person can easily check detection accuracy of the gaze detection apparatus. Accordingly, a situation where a user of the gaze detection apparatus has a feeling of anxious toward a detection result of the gaze detection apparatus can be prevented from occurring.

The above gaze detection apparatus may be configured to further include a first gaze movement detection section and a first prohibition section. After the first display control section displays the first detection result image, the first gaze movement detection section determines whether or not the gaze of the target person is moved based on the result of the detection by the gaze detection section. When the first gaze movement detection section determines that the gaze of the target person is moved, the first prohibition section performs a first prohibition operation which prohibits the first display control section from operating.

It is conceivable that when the first detection result image is displayed while the target person is viewing the display screen, the target person moves his or her gaze to take a look at the first detection result image. Thus, it can be determined that the movement of the gaze after the display of the first detection result image is a response to the display of the first detection result image.

According to the above gaze detection apparatus, after the target person has recognized the first detection result image, the first detection result image is deleted and disappears from the display screen. Because of this, it is possible to prevent an occurrence of the following situation. After the target has recognized the first detection result image, the first detection result image continues to be wastefully displayed on the display screen.

The above gaze detection apparatus may be configured to further include a second display control section that operates to display a preset second detection result image at a particular place when the first gaze movement detection section determines that the gaze of the target person is moved. The particular place is a place where the gaze of the target person and the display screen intersect with each other at a time when the first gaze movement detection section determines that the gaze of the target person is moved. The second detection result image indicates the result of the detection of the gaze of the target person at the time when the first gaze movement detection section determines that the gaze of the target person is moved.

According to the above configuration, when the target person starts moving his or her gaze to check the image indicative of the result of the gaze detection, the display position of the image indicative of the result of the gaze diction is fixed. Because of this, it is possible to prevent an occurrence of the following situation. When the target person tries to check the first detection result image by moving his or her gaze, the first detection result image moves accordingly, and as a result, the target person cannot look fixedly at the first detection result image. Therefore, in the central visual field, the target person can surely check the display position of the first detection result image.

The above gaze detection apparatus may be configured to further include a second prohibition section and a first release section. When a preset display termination determination time has elapsed since the second display control section started displaying the second detection result image, (i) the second prohibition section performs a second prohibition operation which prohibits the second display control section from operating and (ii) the first release section stops the first prohibition section from performing the first prohibition operation, thereby permitting the first display control section to operate.

According to the above configuration, when the display termination determination time has elapsed since the display of the second detection result image was started, the second detection result image is deleted and disappears from the display screen. Because of this, it is possible to prevent an occurrence of the following situation. After the target person has recognized the second detection result image, the second detection result image continues to be wastefully displayed on the display screen. Furthermore, when the display termination determination time has elapsed since the display of the second detection result image was started, control is performed to display the first detection result image based on the result of detection by the gaze detection section. Because of this, the target person can reconfirm the accuracy of the gaze detection apparatus at a different time point.

The above gaze detection apparatus may be configured as follows. The first display control section displays the first detection result image in a first display form. The second display control section displays the second detection result image in a second display form. The first display form and the second display form are different from each other. According to this configuration, from the display forms of the first and second detection result images, the target person can determine whether the image currently-displayed on the display screen to indicate the result of gaze detection is the first detection result image or the second detection result image. In the above, the first detection result image is displayed so as to be movable in response to the movement of the target person's gaze. The first detection result image is fixedly displayed and is not moved in response to the movement of the target person's gaze.

The above gaze detection apparatus may be configured to further include a second gaze position determination section, a third display control section, and a guidance display control section. The second gaze position determination section determines, based on the result of the detection by the gaze detection section, whether or not a screen-outside displayable region lies in the gaze of the target person. The screen-outside displayable region is preset so as to surround the display screen. When the second gaze position determination section determines that the screen-outside displayable region lies in the gaze of the target person, the third display control section displays a third detection result image at a particular place. The particular place is on an outer edge of the display screen and is set in a vicinity of an intersection point between the gaze of the target person and the screen-outside displayable region. The guidance display control section displays a guidance image on the display screen after the third display control section displays the third detection result image, so that the guidance image is located on an opposite side of the third detection result image from the screen-outside displayable region and the guidance image guides the gaze of the target person into the display screen.

According to the above configuration, when the result of detection of the target person's gaze is located in the screen-outside displayable region, the third detection result image is displayed on the outer edge of the display screen so that the third detection result image is located in the vicinity of the position of the target person's gaze. Thereafter, the guidance image is displayed on the display screen. In this way, the target person's gaze is guided, so that the result of detection of the target person's gaze is located inside the display screen. Note that since the guidance image is displayed on the opposite side of the third detection result image from the screen-outside displayable region, the target person trying to take a look at the guidance image moves his or her gaze toward an inside of the display screen.

Because of this, an image indicating the position of the gaze based on the result of detection by the gaze detection section can be displayed on the display screen. Accordingly, the target person can compare (i) the position on the display screen at which he or she is presently actually looking and (ii) the gaze position on the display screen which is based on the result of detection.

If the first detection result image is displayed in a state where the position on the display screen at which he or she is presently actually looking is different from the display position of the first detection result image on the display screen, the target person may recognize the first detection result image with his or her peripheral vision field.

In view of this, the above gaze detection apparatus may be configured such that the first display control section displays the first detection result image in such a display form that the first detection result image visually changes over time. According to this configuration, even if the first detection result image is displayed at a place in the peripheral vision field of the target person, the target person can notice the first detection result image more easily as compared with a case where the first detection result image is displayed in a display form that does not change over time.

The display form that changes over time includes, for example, blinking, size changing, color changing, shape changing, brightness changing and the like.

The above gaze detection apparatus may be configured as follows. The first display control section further displays an allowable error indication image that indicates a range of an allowable gaze detection error of the gaze detection section, wherein a center of the range is at a display position of the first detection result image.

According to the above configuration, the target person can check whether the position on the display screen at which he or she is presently actually looking falls within the range of the allowable gaze detection error, which is centered at the display position of the first or second detection result image. Therefore, the target person can determine that when the position on the display screen at which he or she is presently actually looking falls within the range of the allowable gaze detection error, an error of the gaze detection of the gaze detection section is in the allowable range; otherwise, the error of the gaze detection of the gaze detection section is not in the allowable range.

The above gaze detection apparatus may be mounted to a vehicle and may further include a third prohibition section. When the vehicle is traveling, the third prohibition section prohibits the first gaze position determination section from operating.

According to the above configuration, when the vehicle is stopped, control is performed to display the result of gaze detection on the display screen. Therefore, a driver of the vehicle can check the result of the gaze detection in a state where: the driver is safe even when gazing at the display screen.

The above gaze detection apparatus may be configured to further include a fourth prohibition section that, in response to receipt a preset operation from an external, prohibits the first gaze position determination section from operating.

According to the above configuration, upon receipt of the predetermined operation from an external, the result of gaze detection is prohibited from being displayed on the display screen. As a result, it is possible to prevent an occurrence of the following situation. Even when the target person thinks that confirmation of the result of gaze detection is unnecessary, the result of gaze detection is displayed, and accordingly, the target person has a feeling of discomfort.

The above gaze detection apparatus may be configured to further include a stay time measurement section and a fifth prohibition section. Based on the result of detection by the gaze detection section, the stay time measurement section measures a stay time in which the gaze of the driver stays in a display determination region. The display determination region is preset so as to contain the display screen. When the stay time measured with the stay time measurement section is less than a preset determination prohibition time, the fifth prohibition section prohibits the first gaze position determination section from operating.

According to the above configuration, when the target person gazes at an inside of the display determination region for the determination prohibition time or more, control is performed to display the first detection result image based on the result of detection by the gaze detection section. Because of this, when the target person would like to check the result of gaze detection, the target person can instruct the gaze detection apparatus to display the result of gaze detection on the display screen by performing a simple operation, i.e., fixedly looking at an inside of the display determination region. To do so, the target person needs not perform the predetermined operation.

According to another aspect, a gaze detection method may includes: detecting gaze of a target person; determining, based on a result of the detecting of the gaze of the target person, whether or not a display screen of a display section for displaying an image lies in the gaze of the target person; and displaying a first detection result image at an intersection point between the gaze of the target person and the display screen when it is determined that the display screen lies in the gaze of the target person. The first detection result image is a preset image and indicates the result of the detecting of the gaze of the target person.

The gaze detection method may further comprising: determining, after the first detection result image is displayed, whether or not the gaze of the target person is moved, based on the result of the detecting of the gaze of the target person; and when it is determined that the target person is moved, (i) prohibiting the first detection result image from being displayed and (ii) displaying a preset second detection result image at a particular place. The particular place is a place where the gaze of the target person and the display screen intersect with each other at a time when it is determined that the gaze of the target person is moved. The second detection result image indicates the result of the detecting of the gaze of the target person at the time when it is determined that the gaze of the target person is moved.

The gaze detection method may further include: determining, based on the result of the detecting of the gaze of the target person, whether or not a screen-outside displayable region lies in the gaze of the target person, wherein the screen-outside displayable region is preset so as to surround the display screen; displaying a third detection result image at a particular place when it is determined that the screen-outside displayable region lies in the gaze of the target person, wherein the particular place is on an outer edge of the display screen and is set in a vicinity of an intersection point between the gaze of the target person and the screen-outside displayable region; and displaying a guidance image on the display screen after the third detection result image is displayed, so that the guidance image is located on an opposite side of the third detection result image from the screen-outside displayable region and the guidance image guides the gaze of the target person into the display screen.

The above gaze detection method can achieve substantially the same advantages as the above gaze apparatus.

Although the present invention has been fully described in connection with the above embodiments thereof with reference to the accompanying drawings, it is to be noted that various changes and modifications will become apparent to those skilled in the art. Such changes and modifications are to be understood as being within the scope of the present invention as defined by the appended claims.

What is claimed is:

1. A gaze detection apparatus comprising:
    a gaze detection section that detects gaze of a target person;
    a display section that includes a display screen for displaying an image;
    a first gaze position determination section that operates to determine whether or not the display screen lies in the gaze of the target person based on a result of detection by the gaze detection section;
    a first display control section that operates to display a first detection result image at an intersection point between the gaze of the target person and the display screen when the first gaze position determination section determines that the display screen lies in the gaze of the target person, wherein the first detection result image is a preset image and indicates the result of detection of the target person's gaze, wherein
    the first detection result image moves accordingly with the gaze of the target person, the first display control section further displays an allowable error indication image that indicates a range of an allowable gaze detection error of the gaze detection section, and a center of the allowable error indication image is at a display position of the first detection result image,
    the gaze detection apparatus further comprising:
    a first gaze movement detection section;
    a first prohibition section, wherein
    after the first display control section displays the first detection result image, the first gaze movement detection section determines whether or not the gaze of the target person is moved equal to or more than a preset fixing display determination distance based on the result of the detection by the gaze detection section, and
    when the first gaze movement detection section determines that the gaze of the target person is moved equal to or more than the preset fixing display determination distance, the first prohibition section performs a first prohibition operation which prohibits the first display control section from operating;
    a second gaze position determination section that determines, based on the result of the detection by the gaze detection section, whether or not a screen-outside displayable region lies in the gaze of the target person, wherein the screen-outside displayable region is a preset region surrounding the display screen;
    a third display control section that displays a third detection result image at a particular place when the second gaze position determination section determines that the screen-outside displayable region lies in the gaze of the target person, wherein the particular place is on an outer edge of the display screen and is set in a vicinity of an intersection point between the gaze of the target person and the screen-outside displayable region; and
    a guidance display control section that displays a guidance image on the display screen after the third display control section displays the third detection result image, so that
    the guidance image is located on an opposite side of the third detection result image from the screen-outside displayable region, and
    the guidance image guides the gaze of the target person into the display screen.

2. The gaze detection apparatus according to claim 1, further comprising:
    a second display control section that operates to fixedly display a second detection result image at a particular place when the first gaze movement detection section determines that the gaze of the target person is moved equal to or more than a preset fixing display determination distance, wherein:

the particular place is a place where the gaze of the target person and the display screen intersect with each other at a time when the first gaze movement detection section determines that the gaze of the target person is moved equal to or more than the preset fixing display determination distance;

the second detection result image is a preset image and indicates the result of the detection of the gaze of the target person at the time when the first gaze movement detection section determines that the gaze of the target person is moved equal to or more than the preset fixing display determination distance; and the second display control section further displays an allowable error indication image that indicates a range of an allowable gaze detection error of the gaze detection section, wherein a center of the allowable error indication image is at a display position of the second detection result image.

3. The gaze detection apparatus according to claim 2, further comprising:

a second prohibition section and a first release section, wherein:

when a preset display termination determination time has elapsed since the second display control section started displaying the second detection result image, (i) the second prohibition section performs a second prohibition operation which prohibits the second display control section from operating and (ii) the first release section stops the first prohibition section from performing the first prohibition operation, thereby permitting the first display control section to operate.

4. The gaze detection apparatus according to claim 2, wherein:

the first display control section displays the first detection result image in a first display form;

the second display control section displays the second detection result image in a second display form; and the first display form and the second display form are different from each other.

5. The gaze detection apparatus according to claim 1, wherein:

the first display control section displays the first detection result image in a display form that visually changes over time.

6. The gaze detection apparatus according to claim 1, wherein the gaze detection apparatus is mounted to a vehicle, the gaze detection apparatus further comprising:

a third prohibition section, wherein:

when the vehicle is traveling, the third prohibition section prohibits the first gaze position determination section from operating.

7. The gaze detection apparatus according to claim 1, further comprising:

a fourth prohibition section, wherein in response to receipt of a preset operation from an external, the fourth prohibition section prohibits the first gaze position determination section from operating.

8. The gaze detection apparatus according to claim 1, further comprising:

a stay time measurement section that, based on the result of detection by the gaze detection section, measures a stay time in which the gaze of the driver stays in a display determination region, wherein the display determination region is preset so as to contain the display screen; and a fifth prohibition section that prohibits the first gaze position determination section from operating when the stay time measured with the stay time measurement section is less than a preset determination prohibition time.

9. A gaze detection method comprising:

detecting gaze of a target person;

determining, based on a result of the detecting of the gaze of the target person, whether or not a display screen of a display section for displaying an image lies in the gaze of the target person;

displaying a first detection result image at an intersection point between the gaze of the target person and the display screen when it is determined that the display screen lies in the gaze of the target person, wherein the first detection result image is a preset image and indicates the result of the detecting of the gaze of the target person and the first detection result image moves accordingly with the gaze of the target person;

after displaying the first detection result image, determining whether or not the gaze of the target person is moved equal to or more than a preset fixing display determination distance based on the result of the detecting of the gaze of the target person;

in response to determining that the gaze of the target person is moved equal to or more than the preset fixing display determination distance, (i) prohibiting the first detection result image from being displayed and (ii) fixedly displaying a preset second detection result image at a particular place, wherein the particular place is a place where the gaze of the target person and the display screen intersect with each other at a time when it is determined that the gaze of the target person is moved equal to or more than the preset fixing display determination distance, and the second detection result image indicates the result of the detecting of the gaze of the target person at the time when it is determined that the gaze of the target person is moved equal to or more than a preset fixing display determination distance;

determining, based on the result of the detecting of the gaze of the target person, whether or not a screen-outside displayable region lies in the gaze of the target person, wherein the screen-outside displayable region is preset so as to surround the display screen;

displaying a third detection result image at a particular place when it is determined that the screen-outside displayable region lies in the gaze of the target person, wherein the particular place is on an outer edge of the display screen and is set in a vicinity of an intersection point between the gaze of the target person and the screen-outside displayable region; and displaying a guidance image on the display screen after the third detection result image is displayed, so that the guidance image is located on an opposite side of the third detection result image from the screen-outside displayable region and the guidance image guides the gaze of the target person into the display screen.

* * * * *